(12) United States Patent
Sankai (10) Patent No.: US 10,441,444 B2
(45) Date of Patent: Oct. 15, 2019

(54) MOTION REPRODUCING SYSTEM AND MOTION REPRODUCING APPARATUS

(71) Applicants: CYBERDYNE INC., Tsukuba-shi, Ibaraki (JP); UNIVERSITY OF TSUKUBA, Tsukuba-shi, Ibaraki (JP)

(72) Inventor: Yoshiyuki Sankai, Tsukuba (JP)

(73) Assignees: CYBERDYNE INC., Tsukuba-Shi, Ibaraki (JP); UNIVERSITY OF TSUKUBA, Tsukuba-Shi, Ibaraki (JP)

(*) Notice: Subject to any disclaimer, the term of this patent is extended or adjusted under 35 U.S.C. 154(b) by 388 days.

(21) Appl. No.: 15/319,264

(22) PCT Filed: Jun. 23, 2015

(86) PCT No.: PCT/JP2015/068077
§ 371 (c)(1),
(2) Date: Dec. 15, 2016

(87) PCT Pub. No.: WO2015/199086
PCT Pub. Date: Dec. 30, 2015

(65) Prior Publication Data
US 2017/0143517 A1 May 25, 2017

(30) Foreign Application Priority Data

Jun. 23, 2014 (JP) ................................. 2014-128330

(51) Int. Cl.
*A61B 5/0488* (2006.01)
*B25J 9/00* (2006.01)
(Continued)

(52) U.S. Cl.
CPC .............. *A61F 2/72* (2013.01); *A61B 5/0476* (2013.01); *A61B 5/0488* (2013.01);
(Continued)

(58) Field of Classification Search
CPC combination set(s) only.
See application file for complete search history.

(56) References Cited

U.S. PATENT DOCUMENTS 8,012,107 B2 9/2011 Einav et al.
9,539,162 B2 1/2017 Sankai
(Continued)

FOREIGN PATENT DOCUMENTS

EP 1723941 A1 11/2006
JP 2002-027983 A 1/2002
(Continued)

OTHER PUBLICATIONS

PCT/ISA/210, "International Search Report for International Application No. PCT/JP2015/068077," dated Sep. 15, 2015.
(Continued)

*Primary Examiner* — David H Willse
*Assistant Examiner* — Javier G Blanco
(74) *Attorney, Agent, or Firm* — Manabu Kanesaka (57) ABSTRACT

There is provided a motion reproducing system and a motion reproducing apparatus that store human motions and reproduce them. The motion reproducing system includes a data acquiring apparatus acquiring body motion data representing a motion of a subject during the motion, and transmitting the body motion data, a data managing apparatus receiving the body motion data from the data acquiring apparatus, the data managing apparatus including a memory storing the body motion data, and a motion reproducing apparatus receiving the body motion data stored in the memory from the data managing apparatus, and allowing a reproducer to reproduce the motion of the subject using the body motion data, the motion being performed at the time of acquisition of the body motion data.

3 Claims, 7 Drawing Sheets

(51) Int. Cl.
- *A61H 1/02* (2006.01)
- *A61F 2/72* (2006.01)
- *A61F 2/38* (2006.01)
- *A61B 5/11* (2006.01)
- *B25J 11/00* (2006.01)
- *A61B 5/0476* (2006.01)
- *A61F 2/54* (2006.01)
- *A61F 2/60* (2006.01)
- *B25J 13/08* (2006.01)
- *A61F 5/01* (2006.01)
- *A61F 2/70* (2006.01)
- *A61H 3/00* (2006.01)

(52) U.S. Cl.
CPC ............ *A61B 5/04888* (2013.01); *A61B 5/11* (2013.01); *A61B 5/1121* (2013.01); *A61F 2/38* (2013.01); *A61F 2/54* (2013.01); *A61F 2/60* (2013.01); *B25J 9/0006* (2013.01); *B25J 11/00* (2013.01); *B25J 13/085* (2013.01); *A61F 2002/704* (2013.01); *A61F 2005/0155* (2013.01); *A61H 1/0274* (2013.01); *A61H 1/0277* (2013.01); *A61H 2003/007* (2013.01); *A61H 2201/5069* (2013.01); *A61H 2201/5084* (2013.01)

(56) References Cited

U.S. PATENT DOCUMENTS

| | | | |
|---|---|---|---|
| 2008/0161937 A1* | 7/2008 | Sankai | A61H 3/008 623/25 |
| 2008/0234608 A1* | 9/2008 | Sankai | A61B 5/04888 601/5 |
| 2010/0121232 A1* | 5/2010 | Sankai | A61H 3/008 601/23 |
| 2012/0092286 A1 | 4/2012 | O'Prey et al. | |
| 2015/0217112 A1* | 8/2015 | Shimoda | A61N 1/36003 607/48 |

FOREIGN PATENT DOCUMENTS

| | | | |
|---|---|---|---|
| JP | 2008-080431 A | | 4/2008 |
| JP | 2009-066395 A | | 4/2009 |
| JP | 2009-095382 A | | 5/2009 |
| JP | 2009095382 A | * | 5/2009 |
| JP | 2009-273551 A | | 11/2009 |
| WO | 2005/074371 A2 | | 8/2005 |
| WO | 2009/147875 A1 | | 12/2009 |

OTHER PUBLICATIONS

Europe Patent Office, "Search Report for European Patent Application No. 15812291.1," dated Feb. 2, 2018.

* cited by examiner

MOTION REPRODUCING SYSTEM AND MOTION REPRODUCING APPARATUS

TECHNICAL FIELD

The present invention relates to a motion reproducing system and a motion reproducing apparatus that reproduce motions using body motion data.

BACKGROUND ART

In therapeutic medicine, so-called regenerative medicine has been an active area of research in recent years. Regenerative medicine is a field of medicine in which human body tissues that have been lost to disease or other causes are restored (or regenerated) using the body's own cells, without relying on the use of artificial tissues or transplant from another person or animal (see, e.g., Patent Literature 1). Accordingly, human cell banks are established, in which human cells are cryopreserved for future use.

Regenerative medicine is making it possible to restore human body tissues. However, when motor functions deteriorate due to illness, accident, aging, or the like, it has not been possible to reproduce normal motor functions.

Patent Literature 1: Japanese Unexamined Patent Application Publication No. 2002-27983

SUMMARY OF INVENTION

An object of the present invention is to provide a motion reproducing system and a motion reproducing apparatus that store human motions and reproduce them.

According to one aspect of the present invention, there is provided a motion reproducing system including a data acquiring apparatus acquiring body motion data representing a motion of a subject during the motion, and transmitting the body motion data, a data managing apparatus receiving the body motion data from the data acquiring apparatus, the data managing apparatus including a memory storing the body motion data, and a motion reproducing apparatus receiving the body motion data stored in the memory from the data managing apparatus, and allowing a reproducer to reproduce the motion of the subject using the body motion data, the motion being performed at the time of acquisition of the body motion data.

According to one aspect of the present invention, the data acquiring apparatus is a first wearable motion assisting apparatus including a first frame and a first drive unit, the first frame being worn along a portion between joints of a body of the subject and rotatably connected to the first drive unit. The first wearable motion assisting apparatus includes a first biological signal detector detecting a biological signal generated in accordance with a motion of the subject, a first angular sensor detecting a rotation angle of a joint corresponding to the motion of the subject, a first torque sensor detecting an output torque of the first drive unit, a relative force detector detecting a force acting on the first frame, the force being relatively determined by a relationship between the output torque of the first drive unit and a muscle force of the subject, a first control unit calculating an assist force to be applied from the first drive unit to the first frame on the basis of the output torque of the first drive unit, the biological signal, the rotation angle, and the force acting on the first frame, and a first communicating unit transmitting the output torque of the first drive unit, the biological signal, the rotation angle, and the force acting on the first frame as the body motion data to the data managing apparatus.

According to one aspect of the present invention, the motion reproducing apparatus is a second wearable motion assisting apparatus including a second frame and a second drive unit, the second frame being worn along a portion between joints of a body of the reproducer and ratatably connected to the second drive unit. The second wearable motion assisting apparatus includes a second biological signal detector detecting a biological signal generated in accordance with a motion of the reproducer, a second angular sensor detecting a rotation angle of a joint corresponding to the motion of the reproducer, a second torque sensor detecting an output torque of the second drive unit, a second communicating unit receiving the body motion data from the data managing apparatus, and a second control unit calculating an assist control output torque on the basis of, of the body motion data, the output torque of the first drive unit, the biological signal detected by the first biological signal detector, the rotation angle detected by the first angular sensor, and the force acting on the first frame, calculating an angle control output torque for making equal the rotation angle detected by the first angular sensor and the rotation angle detected by the second angular sensor, and calculating an assist force to be applied from the second drive unit to the second frame on the basis of the assist control output torque and the angle control output torque.

According to one aspect of the present invention, the second control unit calculates a force control output torque for making equal or proportional the output torque of the second drive unit and the output torque of the first drive unit included in the body motion data, and calculates the assist force to be applied from the second drive unit to the second frame on the basis of the assist control output torque, the angle control output torque, and the force control output torque.

According to one aspect of the present invention, the motion reproducing apparatus is an embedded-type motion assisting apparatus embedded in one of four limbs of the reproducer. The embedded-type motion assisting apparatus includes a first limb coupled to a first bone, a second limb coupled to a second bone, a third angular sensor detecting a pivoting angle of the second limb with respect to the first limb, a third drive unit disposed between the first limb and the second limb, and configured to drive the second limb with respect to the first limb in a rotation direction of a joint, a third communicating unit receiving the body motion data, and a third control unit calculating an output torque for making equal the pivoting angle detected by the third angular sensor and the rotation angle detected by the first angular sensor and included in the body motion data, and controlling the third drive unit.

According to one aspect of the present invention, the data acquiring apparatus is a motion capture apparatus, and is configured to acquire a rotation angle of a joint of the subject as the body motion data.

According to one aspect of the present invention, the data managing apparatus includes a billing function unit configured to bill the motion reproducing apparatus when a request to send out the body motion data stored in the memory is received from the motion reproducing apparatus.

According to one aspect of the present invention, there is provided a motion reproducing apparatus configured to receive body motion data representing a motion of a subject from a data managing apparatus storing the body motion data, and allow a reproducer to reproduce the motion of the subject using the body motion data, the motion being performed when the body motion data was acquired.

According to one aspect of the present invention, the motion reproducing apparatus is a wearable motion assisting apparatus including a frame and a drive unit, the frame being worn along a portion between joints of a body of the reproducer and ratatably connected to the drive unit. The wearable motion assisting apparatus includes a biological signal detector detecting a biological signal generated in accordance with a motion of the subject, an angular sensor detecting a rotation angle of a joint corresponding to the motion of the subject, a torque sensor detecting an output torque of the drive unit, a communicating unit receiving the body motion data from the data managing apparatus, and a control unit calculating an assist control output torque on the basis of, of the body motion data, the output torque of the drive unit, the biological signal detected by the biological signal detector, the rotation angle detected by the angular sensor, and a force acting on the frame, calculating an angle control output torque for making equal the rotation angle detected by the angular sensor and a target rotation angle, and calculating an assist force to be applied from the drive unit to the frame on the basis of the assist control output torque and the angle control output torque.

According to one aspect of the present invention, the reproducer is a robot.

Advantageous Effects of Invention

According to the present invention, it is possible to store and manage human body motion data and reproduce human motions on the basis of the body motion data.

DESCRIPTION OF EMBODIMENTS

Embodiments of the present invention will now be described on the basis of the drawings.

Figure 1:
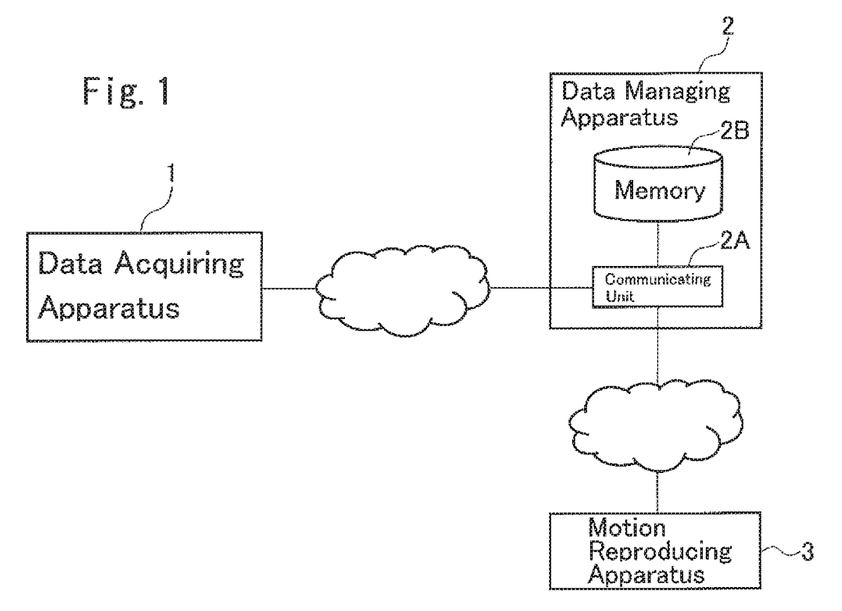
FIG. 1 is a schematic view of a body motion reproducing system according to an embodiment of the present invention.

FIG. 1 is a schematic view of a body motion reproducing system according to an embodiment of the present invention. As illustrated in FIG. 1, the body motion reproducing system includes a data acquiring apparatus 1 configured to acquire body motion data from a user (subject), a data managing apparatus 2 configured to store and manage the body motion data acquired by the data acquiring apparatus 1, and a motion reproducing apparatus 3 configured to allow the user to reproduce his or her own body motion using the body motion data.

The body motion data is data that represents user's motions, such as standing up, walking, going up and down stairs, bending and stretching the knees and elbows, and turning the shoulder and hip. Examples of the body motion data include a biological signal, such as a biopotential (biopotential signal) on the skin surface or brain waves, joint angle, angular speed, acceleration, the position of the center of gravity of the body, and marker positions obtained by motion capture. The biopotential signal represents the amount of force by which each part of the body is moved. The joint angle, angular speed, and acceleration represent the speed and range of motion of each part of the body.

The data acquiring apparatus 1 acquires body motion data representing various motions performed by the user, and transmits the acquired body motion data to the data managing apparatus 2. The data managing apparatus 2 includes a communicating unit 2A and a memory 2B. The body motion data received from the data acquiring apparatus 1 by the communicating unit 2A is stored in the memory 2B. In response to a request from the motion reproducing apparatus 3, the communicating unit 2A transmits the user's body motion data to the motion reproducing apparatus 3.

The motion reproducing apparatus 3 uses the user's body motion data received from the data managing apparatus 2 to allow the user to reproduce his or her own body motion performed at the time of acquisition of the body motion data. For example, body motion data is acquired and stored when the user is in good health. Then, when motor functions of the user deteriorate due to illness, accident, or aging, the body motion data is used to allow the user to reproduce his or her own body motion performed when he or she was in good health, so that the motor functions can be improved.

FIG. 1 illustrates an example in which the data acquiring apparatus 1 and the data managing apparatus 2, and the data managing apparatus 2 and the motion reproducing apparatus 3, are connected to each other via a network for transmission and reception of body motion data. Alternatively, data may be recorded in a transportable recording medium, such as a CD-ROM, for giving and receiving the data.

Figure 2:
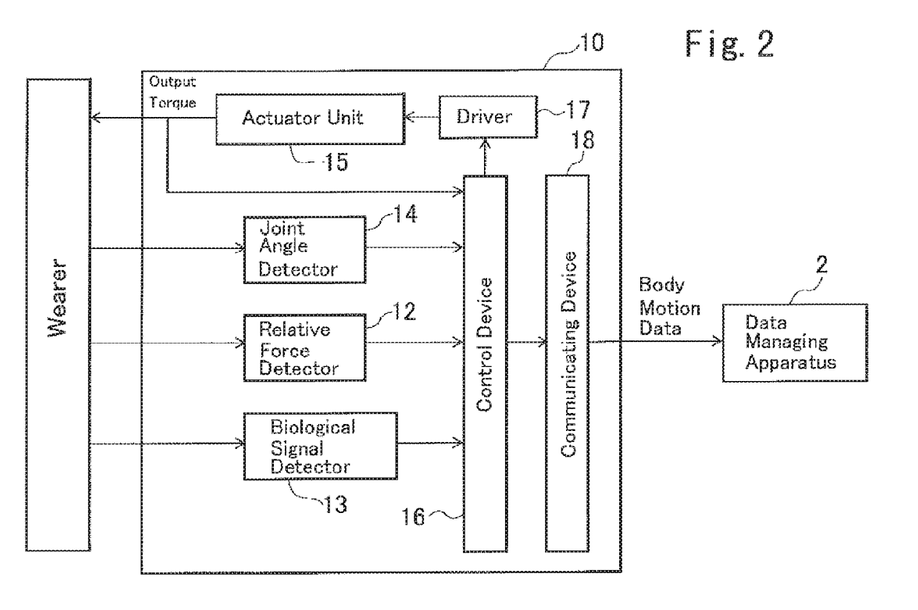
FIG. 2 is a block diagram illustrating a control system of a data acquiring apparatus according to the embodiment.
Figure 3:
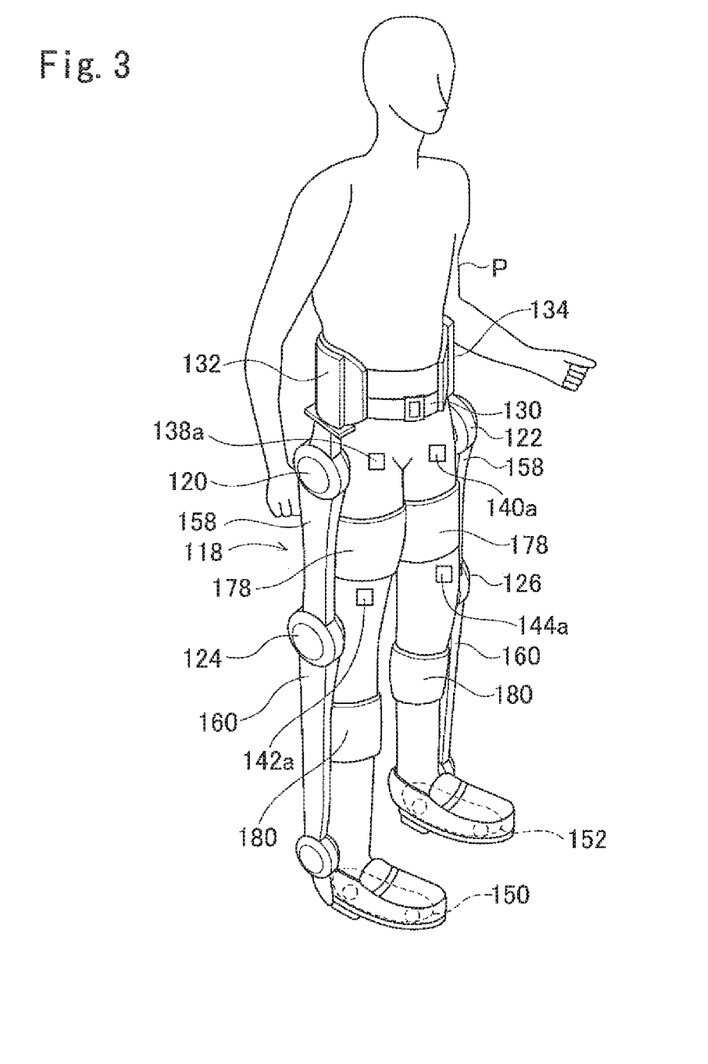
FIG. 3 is an external perspective view of a wearable motion assisting apparatus.
Figure 4:
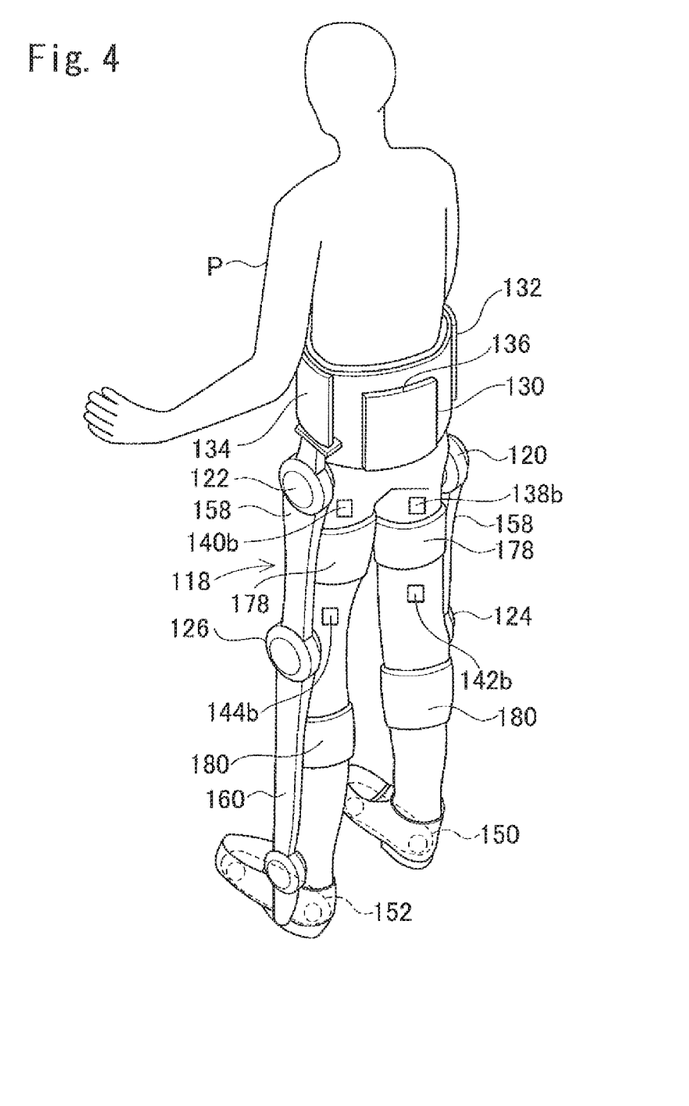
FIG. 4 is another external perspective view of the wearable motion assisting apparatus.
Figure 5:
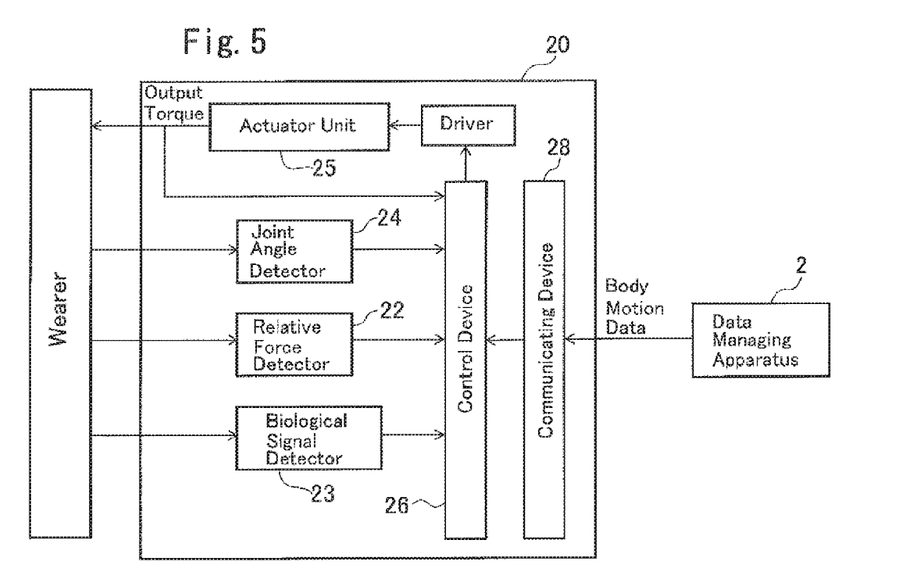
FIG. 5 is a block diagram illustrating a control system of a motion reproducing apparatus according to the embodiment.

The data acquiring apparatus 1 that acquires body motion data of the user, and the motion reproducing apparatus 3 that reproduces a body motion of the user using the body motion data, will now be described. In the present embodiment, a wearable motion assisting apparatus illustrated in FIGS. 2 to 4 is used as the data acquiring apparatus 1. FIG. 2 is a block diagram illustrating a configuration of a control system of a wearable motion assisting apparatus serving as the data acquiring apparatus 1. FIG. 3 is a perspective view of the wearable motion assisting apparatus worn by the user, as viewed from the front side, and FIG. 4 is a perspective view of the same, as viewed from the back side. A wearable motion assisting apparatus having a configuration similar to that of the data acquiring apparatus 1 may be used as the motion reproducing apparatus 3. FIG. 5 is a block diagram illustrating a configuration of a control system of a wearable motion assisting apparatus serving as the motion reproducing apparatus 3. The wearable motion assisting apparatus in FIG. 5 has the same appearance as that illustrated in FIGS. 3 and 4.

A wearable motion assisting apparatus is obtained by pivotably (rotatably) connecting a frame worn along a portion (e.g., hip, thigh, or shank) between joints of a human body (wearer's body) to an actuator unit. Although the wearable motion assisting apparatus illustrated in FIGS. 3 and 4 is a lower-body wearable motion assisting apparatus having actuator units for knee joints and hip joints, an upper-body or whole-body wearable motion assisting apparatus may be used in the present invention.

A wearable motion assisting apparatus 10 worn by the user and serving as the data acquiring apparatus 1 is configured to acquire, as body motion data, a physical phenomenon detection signal, such as a joint angle value and an output torque value, of the wearable motion assisting apparatus 10 and a biological signal (e.g., a biopotential signal or brain waves) generated when the wearer moves muscles around a joint, and then to transmit the acquired body motion data to the data managing apparatus 2.

As illustrated in FIG. 2, the wearable motion assisting apparatus 10 includes a relative force detector 12, a biological signal detector 13, a joint angle detector 14, an actuator unit 15, a control device 16, a driver 17, and a communicating device 18.

The relative force detector 12 is configured to detect a force acting on the frame of the wearable motion assisting apparatus 10, that is, a force (relative force) relatively determined by the relationship between the output torque of the actuator unit 15 serving as a drive source and the muscle force of the wearer. For example, the relative force detector 12 is a force sensor.

The relative force is a force acting on the frame. The relative force represents the amount of force received by the wearer from the output torque of the actuator unit 15, that is, the amount of assist received by the wearer.

The force sensor is configured to measure a force acting on the frame. For example, the force sensor is formed by a strain gauge that detects a strain corresponding to an applied force and outputs an electrical signal proportional to the amount of generated strain. The frame is provided with the force sensor at a portion thereof where deflection occurs under the drive torque of the actuator unit 15.

The biological signal detector 13 is a biological signal detecting means that detects a biological signal (e.g., a biopotential signal or brain waves) generated when the wearer wearing the wearable motion assisting apparatus 10 moves muscles around a joint. For example, a biopotential sensor is used as the biological signal detector 13 in the present embodiment. Also in the present embodiment, the biopotential sensor is affixed to the skin surface around the joint of the wearer, with an adhesive seal covering the periphery of the sensor. In the present embodiment, a signal obtained from a signal detected by the biopotential sensor affixed to the skin surface around the joint of the wearer (i.e., around muscles that act when the joint is moved) is referred to as a biopotential signal.

The joint angle detector 14 is configured to detect the rotation angle of a knee joint of the wearer. For example, an angular sensor is used as the joint angle detector 14. The angular sensor is formed, for example, by a rotary encoder that counts the number of pulses proportional to the joint angle of the wearable motion assisting apparatus 10. As a sensor output, the angular sensor outputs an electrical signal corresponding to the number of pulses proportional to the joint angle. Specifically, the angular sensor detects a pivoting angle between two frames coupled to the actuator unit 15.

The control device 16 calculates an output torque value on the basis of the joint angle and the output torque of the wearable motion assisting apparatus 10, the biopotential signal, and the relative force. The calculated output torque value represents the value of torque to be output from the actuator unit 15. Then, the control device 16 supplies a signal corresponding to the calculated output torque value to the driver 17.

The driver 17 is configured to supply power to the actuator unit 15 such that a torque corresponding to the output torque value output from the control device 16 is output from the actuator unit 15. In the present embodiment, the driver 17 supplies a drive current corresponding to the output torque value to a power unit of the actuator unit 15.

The actuator unit 15 is configured to apply, to a frame pivotally (rotatably) connected to the actuator unit 15, an output torque based on the drive current supplied from the driver 17 as an assist force. Here, the assist force is a force acting about the actuator unit 15 (which serves as a rotation axis) provided at the position corresponding to the joint of the wearer. The assist force may also be referred to as an assist torque. The assist torque of the actuator unit 15 is fed back to the control device 16. In the present embodiment, the actuator unit 15 is formed by an electric power unit serving as a drive source, and a gear mechanism configured to transmit the rotational drive force of the power unit at a reduced speed.

The communicating device 18 is formed by a communicating means including communication equipment, such as a communication modem or router connected to a public line or the Internet. The communicating device 18 transmits various types of data, such as the output torque value and the joint angle, obtained by the wearable motion assisting apparatus 10 to the data managing apparatus 2 as body motion data.

As illustrated in FIG. 5, a wearable motion assisting apparatus 20 serving as the motion reproducing apparatus 3 includes a relative force detector 22, a biological signal detector 23, a joint angle detector 24, an actuator unit 25, a control device 26, a driver 27, and a communicating device 28. The relative force detector 22, the biological signal detector 23, the joint angle detector 24, the actuator unit 25, the control device 26, the driver 27, and the communicating device 28 are configured in substantially the same manner as the relative force detector 12, the biological signal detector 13, the joint angle detector 14, the actuator unit 15, the control device 16, the driver 17, and the communicating device 18 of the wearable motion assisting apparatus 10. Differences from these components of the wearable motion assisting apparatus 10 will be described.

The communicating device 28 receives, from the data managing apparatus 2, body motion data previously acquired from the user using the wearable motion assisting apparatus 10. The body motion data received here includes, for example, a joint angle and an output torque.

The control device 26 calculates an output torque value on the basis of the joint angle and the output torque of the wearable motion assisting apparatus 20, the body motion data (including the joint angle and the output torque) received from the data managing apparatus 2, and a biopotential signal and a relative force detected by the wearable motion assisting apparatus 20. The output torque value calculated here represents the value of torque to be output from the actuator unit 25.

As illustrated in FIGS. 3 and 4, when a wearer P wearing the wearable motion assisting apparatuses 10 and 20 performs a voluntary motion, a drive torque corresponding to a biological signal generated at the time of the motion is applied to the wearer P as an assist force. This allows the wearer P to walk while supporting his or her full weight using the resultant of his or her muscle force and the drive torque of the actuator units 15 and 25 (electric power units are used in the present embodiment).

The wearable motion assisting apparatuses 10 and 20 perform control such that the assist force (power unit torque) applied in accordance with a detection signal from the biopotential sensor and a shift in the center of gravity associated with the walking motion reflects the intention of the wearer P, as described below. Accordingly, the actuators of the wearable motion assisting apparatuses 10 and 20 are controlled not to apply a load against the intention of the wearer P, and are controlled not to interfere with the motion of the wearer P.

The wearable motion assisting apparatuses 10 and 20 are capable of providing powered assist to various motions, such as walking, rising up from a chair, sitting down on a chair, and going up and down stairs.

The wearable motion assisting apparatuses 10 and 20 are each obtained by adding a drive unit to a frame mechanism 118 worn by the wearer P. The drive unit includes a right-thigh drive power unit 120 located at the right hip joint of the wearer P, a left-thigh drive power unit 122 located at the left hip joint of the wearer P, a right-knee drive power unit 124 located at the right knee joint of the wearer P, and a left-knee drive power unit 126 located at the left knee joint of the wearer P. These drive power units 120, 122, 124, and 126 are each formed by an electric power unit including a DC or AC motor whose drive torque is controlled by a control signal from the control device. The drive power units 120, 122, 124, and 126 each include a speed reducing mechanism (housed in the drive unit) configured to reduce the speed of the motor rotation at a predetermined reduction rate, and are small but capable of applying a sufficient drive force. A low-profile ultrasonic motor may be used as a drive power unit to save installation space.

The rotation shafts of the drive power units 120, 122, 124, and 126 are each configured to transmit the drive torque through the gear mechanism to first frames 158 and second frames 160 on the driven side. The first frames 158 are each formed to extend along the outside of the corresponding thigh of the wearer P, and the second frames 160 are each formed to extend blow the corresponding first frame 158 and along the outside of the corresponding shank of the wearer P.

Belt-like thigh fastening members 178 each configured to be fastened to the corresponding thigh of the wearer P is attached to the intermediate position of the first frame 158 in the longitudinal direction. Belt-like shank fastening members 180 each configured to be fastened to the corresponding shank below the knee of the wearer P is attached to the intermediate position of the second frame 160 in the longitudinal direction. Accordingly, the drive torque generated by the drive power units 120, 122, 124, and 126 is transmitted through the gear to the first frames 158 and the second frames 160, and is further transmitted through the thigh fastening members 178 and the shank fastening members 180 as an assist force to the legs of the wearer P.

Batteries 132 and 134 each serving as a power source for driving the drive power units 120, 122, 124, and 126 are attached to a belt-like hip fastening member 130 worn on the hip of the wearer P. The batteries 132 and 134 are rechargeable batteries, and are separately placed on the right and left, so as not to interfere with the motion of the wearer P.

A control unit 136 is attached to the back side of the hip fastening member 130, which is on the back of the wearer P. The control unit 136 includes the control devices 16 and 26 and the communicating devices 18 and 28 described above.

The biological signal detectors 13 and 23 include biological signal sensors 138a and 138b configured to detect a biopotential associated with the motion of the right thigh of the wearer P, biological signal sensors 140a and 140b configured to detect a biopotential associated with the motion of the left thigh of the wearer P, biological signal sensors 142a and 142b configured to detect a biopotential associated with the motion of the right knee of the wearer P, and biological signal sensors 144a and 144b configured to detect a biopotential associated with the motion of the left knee of the wearer P.

These biological signal sensors 138a, 138b, 140a, 140b, 142a, 142b, 144a, and 144b are each a biological signal detecting means that detects a biological signal, such as a myoelectric potential signal or a neurotransmitter signal, through the skin and include a sensor (not shown) for detecting a faint potential. In a human body, acetylcholine acting as a synaptic transmitter is released by a command from the brain onto the surface of muscles forming skeletal muscles, and this changes the ionic permeability of the sarcolemmal membrane to generate an action potential. The action potential causes contraction of muscle fibers, and generates a muscle force. Therefore, detecting the potential of the skeletal muscles makes it possible to estimate a muscle force generated during a motion. Then, from a virtual torque based on the estimated muscle force, an assist force required for the motion can be determined.

The control devices 16 and 26 are thus configured to determine a drive current to be supplied to the four drive power units 120, 122, 124, and 126 on the basis of biological signals detected by the biological signal sensors 138a, 138b, 140a, 140b, 142a, 142b, 144a, and 144b, and drive the drive power units 120, 122, 124, and 126 with the determined drive current, thereby providing an assist force to assist the motion of the wearer P.

The drive power units 120, 122, 124, and 126 include the joint angle detectors 14 and 24 each configured to detect a joint angle. The joint angle detectors 14 and 24 are each formed by an angular sensor, such as a rotary encoder that counts the number of pulses proportional to a joint angle. The joint angle detectors 14 and 24 are each configured to output, as a sensor output, an electrical signal corresponding to the number of pulses proportional to the joint angle.

For smooth shifting of the center of gravity, it is necessary to detect a load applied to the bottom of each foot to detect the position of the center of gravity. Accordingly, load measuring units 150 and 152 (indicated by broken lines in FIGS. 3 and 4) each configured to measure the load at two or more points on the bottom of the foot are attached to the bottom surfaces of the right and left feet of the wearer P. The load measuring units 150 and 152 are firmly held to the respective bottom surfaces of the feet, and configured to detect a reactive force that varies in accordance with the shifting of body weight associated with a walking action.

The control device 16 of the wearable motion assisting apparatus 10 calculates an assist control output torque on the basis of the output torque of the actuator unit of the wearable motion assisting apparatus 10, a joint angle, a relative force acting on a frame, and a biological signal (e.g., including a myoelectric potential signal, a neurotransmitter signal, and brain waves) generated by the wearer P, and outputs the calculated assist control output torque through the driver to the motor. The control device 16 estimates the wearer's motion intention on the basis of such information as a joint angle and an acceleration detected by an acceleration sensor, generates an autonomic command signal for causing the actuator unit to generate power in accordance with the intention, and calculates an assist control output torque using the autonomic command signal. The autonomic command signal based on the joint angle and the acceleration makes it possible to perform gravity compensation of the frames of the wearable motion assisting apparatus 10 and viscosity compensation of the drive power units. Therefore, without feeling the weight of the wearable motion assisting apparatus 10, the wearer can move in the same manner as when not wearing the wearable motion assisting apparatus 10. Thus, body motion data acquired by the wearable motion assisting apparatus 10 serving as the data acquiring apparatus 1 reflects the natural motion of the wearer.

The control device 26 of the wearable motion assisting apparatus 20 calculates an angle control output torque, a force control output torque, and an assist control output torque, and outputs an output torque obtained by adding up these torques through the driver to the motor. The angle control output torque is an output torque for making equal a joint angle and a joint angular speed included in body motion data received from the data managing apparatus 2 and a joint angle and a joint angular speed of the wearable motion assisting apparatus 20. The force control output torque is an output torque for making equal or proportional an output torque included in the body motion data received from the data managing apparatus 2 and an output torque on the side of the wearable motion assisting apparatus 20. The assist control output torque is calculated on the basis of the output torque and the joint angle of the wearable motion assisting apparatus 20, a biopotential, and a relative force.

By outputting the output torque obtained by adding up the angle control output torque, the force control output torque, and the assist control output torque to the motor, a motion represented by the body motion data received from the data managing apparatus 2 can be reflected in the motion of the wearer of the wearable motion assisting apparatus 20.

The user can acquire normal body motion data and store it in the data managing apparatus 2 by performing various motions, such as walking and bending and stretching, while wearing the wearable motion assisting apparatus 10 when he or she is in good health. Then, if motor functions deteriorate due to illness, accident, aging, or the like, the user can reproduce his or her own motions performed when he or she was in good health by wearing the wearable motion assisting apparatus 20 and supplying his or her body motion data stored in the data managing apparatus 2 to the control device 26.

Thus, even when motor functions deteriorate, the user can improve the motor functions through treatment and rehabilitation while feeling, and aiming to restore, his or her own normal motions performed when he or she was in good health. When the acquired body motion data is extracted to reproduce motions, various motions performed at the time of acquisition of the body motion data can be reproduced without additional operations. As for motions not performed at the time of acquisition of the body motion data, body motion data related to the required motions is partly used (or used in combination), so that any motions can be reproduced.

Although the wearable motion assisting apparatus 10 and the wearable motion assisting apparatus 20 are configured in the same manner in the embodiment described above, they may be configured in different manners. For example, the wearable motion assisting apparatus 10 serving as the data acquiring apparatus 1 may be configured to acquire body motion data including joint angles of both legs as illustrated in FIGS. 3 and 4, whereas the wearable motion assisting apparatus 20 serving as the motion reproducing apparatus 3 may have only the right or left leg with a deteriorated motor function.

Figure 6:
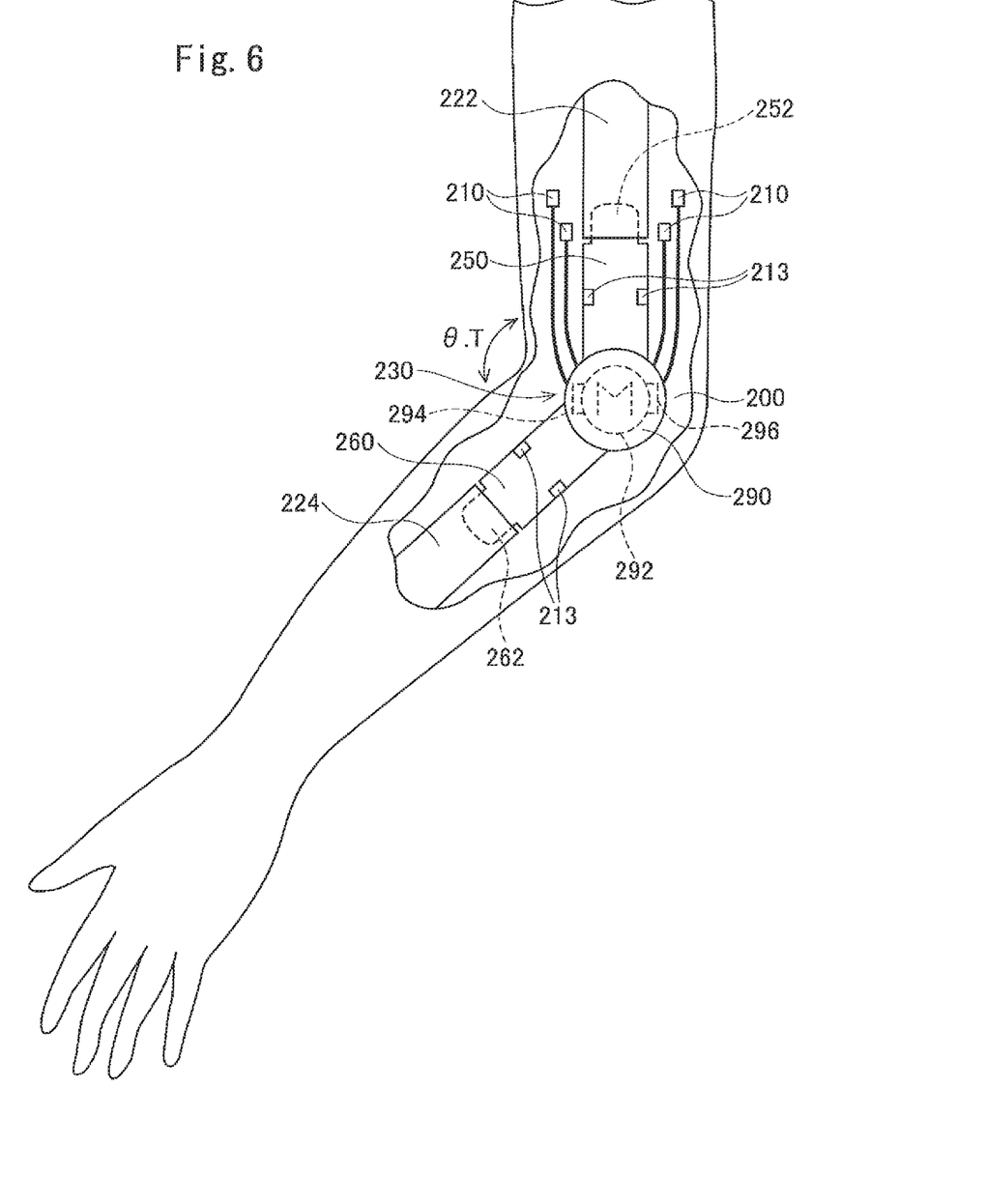
FIG. 6 is a schematic view of an embedded-type motion assisting apparatus.

The motion reproducing apparatus 3 may be a motion assisting apparatus of an embedded type, instead of the wearable type. FIG. 6 illustrates an embedded-type motion assisting apparatus. Although FIG. 6 illustrates a motion assisting apparatus embedded in an elbow joint of an arm, which is one of four limbs, the motion assisting apparatus may be embedded in each of joints in elbows of both arms and knees of both legs.

As illustrated in FIG. 6, the embedded-type motion assisting apparatus is an apparatus configured to assist the motion of the joint, and includes a motion assisting unit 230 worn on a joint 200 of the wearer. The motion assisting unit 230 includes a first limb 250 coupled to a first bone 222 formed by an upper-arm bone of the joint 200 of the elbow, a second limb 260 coupled to a second bone 224 composed of the radius on the thumb side and the ulna on the little-finger side and located below the elbow of the joint 200, a motor unit (driving means) 290 disposed between the first limb 250 and the second limb 260 and configured to drive the second limb 260 with respect to the first limb 250 in the rotation direction of the joint. A coupling portion 252 coupled to the first bone 222 protrudes from the upper end of the first limb 250. A coupling portion 262 coupled to the second bone 224 protrudes from the lower end of the second limb 260.

The coupling portions 252 and 262 of the first limb 250 and the second limb 260 are directly coupled to the respective bones, and thus are formed of a corrosion-resistant material, such as titanium, titanium alloy, or ceramics.

A control unit (not shown) that supplies a drive current to the motor unit 290 and a communication device (not shown) that receives body motion data from the data managing apparatus 2 are provided to the side of the motor unit 290. The motor unit 290 includes an electric motor 292 formed by a DC or AC motor. The drive force of the electric motor 292 is transmitted as a relative rotation between the stator and the rotator, through a speed reducing mechanism such as a speed reducing gear, to the second limb 260.

The control unit is formed by a microcomputer. The control unit generates a drive current and supplies it to a coil of the electric motor 292 to cause the second limb 260 to pivot with respect to the first limb 250.

Biopotential sensors 210 (biological signal detecting means) that detect the biopotential of the upper arm portion are connected to the control unit of the motor unit 290. When the wearer tries to move an arm, the nervous system extending from the brain generates a neurotransmitter signal. This allows the biopotential sensors 210 to directly detect a biopotential signal, such as a myoelectric potential signal or a neurotransmitter signal, without involving passing through the skin.

The first limb 250 and the second limb 260 are each internally provided with a rechargeable battery unit. The rechargeable battery unit is composed of a charging unit that externally performs non-contact charging and rechargeable batteries.

The motor unit 290 includes a torque sensor 294 configured to detect a torque T generated by the supplied drive current, and an angular sensor 296 configured to detect a pivoting angle $\theta$ between the first limb 250 and the second limb 260. The torque sensor 294 and the angular sensor 296 output detection signals representing the detected torque and the detected angle to the control unit of the motor unit 290. Examples of the torque sensor 294 include a magnetostrictive torque sensor configured to detect a strain in the shaft that transmits the rotational drive force, and an electromagnetic torque sensor configured to electromagnetically detect a phase difference between a drive-side gear and a load-side gear of the motor 292. Examples of the angular sensor 296 include a rotary encoder configured to count the number of pulses corresponding to the rotation angle, and a potentiometer configured to vary a resistance value in accordance with the rotation angle.

The outer periphery of each of the first limb 250 and the second limb 260 is provided with stress sensors 213 each configured to detect a stress that acts when the motor is driven. The stress sensors 213 are each formed by a strain gauge, and configured to output a detection signal corresponding to a stress acting on the corresponding one of the first limb 250 and the second limb 260 to the control unit of the motor unit 290.

The control unit determines a neurotransmitter signal and a myoelectric potential signal from biopotentials detected by the biopotential sensors 210, and determines an assist control output torque value for causing the motor unit 290 to generate power in accordance with the wearer's intention. Also, the control unit determines an angle control output torque for making equal a joint angle and a joint angular speed included in body motion data received from the data managing apparatus 2 and a joint angle and a joint angular speed detected by the angular sensor 296. Additionally, the control unit determines a force control output torque for making equal or proportional an output torque included in the body motion data received from the data managing apparatus 2 and an output torque of the embedded-type motion assisting apparatus. Then, the control unit outputs, to the motor 292, an output torque obtained by adding up the angle control output torque, the force control output torque, and the assist control output torque. Thus, a motion represented by the body motion data stored in the data managing apparatus 2 is reflected in the motion of the user of the embedded-type motion assisting apparatus.

As described above, even when the embedded-type motion assisting apparatus is used as the motion reproducing apparatus 3, it is possible to reproduce a motion performed when the user was in good health.

Figure 7:
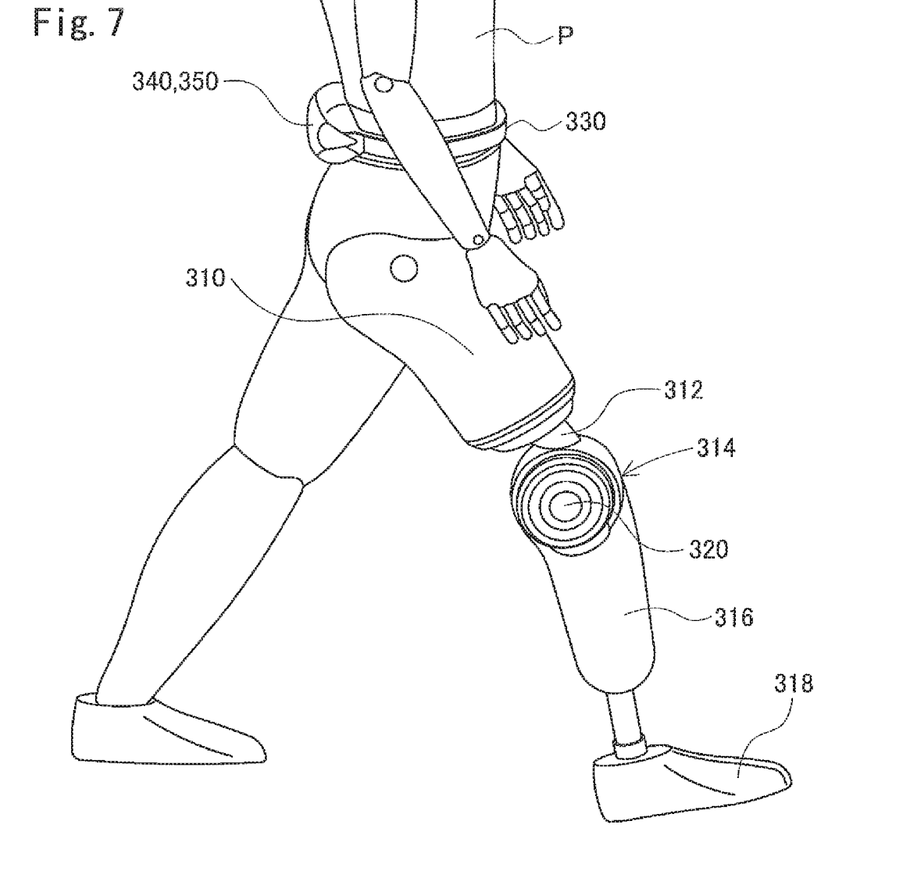
FIG. 7 is a schematic view of an artificial-leg-type motion assisting apparatus.

The motion reproducing apparatus 3 may be an artificial limb. FIG. 7 illustrates an artificial-leg-type motion assisting apparatus attached to the thigh of the amputated right leg of the wearer P and functioning as the motion reproducing apparatus 3. This motion assisting apparatus includes a socket 310, a thigh frame 312, a knee joint portion 314, a lower leg frame 316, and a foot portion 318.

The socket 310 is internally provided with an insertion recess formed to accommodate the shape of the right thigh, and is molded of a resin or the like. For example, after the stump of the amputated right thigh of the wearer P is fitted into the insertion recess of the socket 310, air between the stump and the socket 310 is removed and a negative pressure is applied to the socket 310. The socket 310 is thus worn by the wearer P.

One end of the thigh frame 312 is coupled through an attachment (not shown) to the socket 310, and the other end of the thigh frame 312 is coupled to the knee joint portion 314. The thigh frame 312 is provided with an absolute angle sensor that detects the angle of the hip joint with respect to the vertical direction. The absolute angle sensor calculates the absolute angle (hip joint angle) between the hip joint (thigh) and the vertical direction by using an acceleration sensor in the case of a low-frequency motion, and using a gyroscope in the case of a high-frequency motion.

The knee joint portion 314 functions as the right knee joint of the wearer P. The other end of the thigh frame 312 is coupled to one side of the knee joint portion 314, and one end of the lower leg frame 316 is coupled to the other side of the knee joint portion 314. The knee joint portion 314 allows the thigh frame 312 and the lower leg frame 316 to be pivotally (rotatably) coupled to each other. The knee joint portion 314 is provided with a drive unit 320. The drive unit 320 is formed by an electric motor, and configured to directly drive the knee joint portion 314. This allows the knee joint to actively bend and stretch. The drive unit 320 is provided with an angular sensor (not shown) that detects the angle (bending angle) of the knee joint. For example, this angular sensor is a potentiometer.

The other end of the lower leg frame 316 is coupled to the foot portion 318. An energy-storage-type foot portion capable of using stored energy for kicking out is used as the foot portion 318. The energy is stored in the foot portion 318 mainly by the elastic force of a carbon plate when the right leg serves as a support leg.

A biological signal sensor (not shown) configured to detect a biopotential (biological signal) in the thigh of the right leg is affixed to each of the front and back skin surfaces of the thigh of the right leg of the wearer P.

A hip belt 330 is worn on the hip of the wearer P. A control unit 340 and a battery 350 are mounted on the back side of the hip belt 330. The control unit 340 acquires a detection result from each sensor to control the drive unit 320. The battery 350 supplies power to the control unit 340 and each sensor.

The control unit 340 acquires body motion data from the data managing apparatus 2, calculates an output torque in the same manner as above, and outputs the output torque from the electric motor of the drive unit 320. Thus, a motion represented by the body motion data stored in the data managing apparatus 2 is reflected in the motion of the wearer of the artificial leg.

In the embodiments described above, the motion reproducing apparatus 3 outputs a torque to the motor to provide an assist force to the user, thereby reproducing a normal motion performed when the user was in good health. Alternatively, the normal motion may be reproduced by applying electrical stimulation to muscles. In this case, the angular sensor detects the joint angle and the joint angular speed of the user of the motion reproducing apparatus 3, and electrical stimulation is applied to muscles such that the detected joint angle and joint angular speed match the body motion data. Also, the motion reproducing apparatus 3 performs a interpolation computation of a time lag between the time of acquisition of body motion data and the time of reproduction of the body motion data using the results of vital sensing and medical checkup history of a subject, and performs a motion balance adjustment required due to a decline in physical strength over time.

A motion capture apparatus may be used as the data acquiring apparatus 1. The motion capture apparatus continuously photographs a user having markers attached to predetermined body portions thereof with an infrared camera or the like, calculates the loci of the markers using the photographed successive images, and thus acquires body motion data including the position, speed, and acceleration of each body portion of the user. This body motion data is stored in the data managing apparatus 2 and used when the motion reproducing apparatus 3 reproduces motions.

In the embodiments described above, the motion reproducing apparatus 3 reproduces motions using user's own body motion data stored in the data managing apparatus 2. Alternatively, another person's motions may be reproduced using body motion data of the person. That is, a subject whose body motion data is acquired may differ from a motion reproducer who uses the body motion data. For example, the data acquiring apparatus 1 acquires body motion data of a professional athlete and stores it in the data managing apparatus 2. The user can acquire the body motion data of the professional athlete from the data managing apparatus 2, and feel the motions of the professional athlete.

By considering the difference in physical ability between the motion reproducer and the professional athlete, the motion reproducing apparatus 3 may set a stepwise menu according to the motion of the professional athlete, and allow the motion reproducer to feel the motion while reducing the load on the heart of the motion reproducer.

The motion reproducing apparatus 3 may cause a machine, such as a robot, to reproduce a motion using human body motion data stored in the data managing apparatus 2. For example, the data acquiring apparatus 1 acquires body motion data of a professional athlete and stores it in the data managing apparatus 2. The user can acquire the body motion data of the professional athlete from the data managing apparatus 2, and cause one or more robots connected to the motion reproducing apparatus 3 to reproduce motions of the professional athlete. Each robot may include the motion reproducing apparatus 3.

The data managing apparatus 2 may include a billing function unit for billing when a request to send out body motion data stored in the memory 2B is received from the motion reproducing apparatus 3. For example, the billing function unit has an online card transaction function using credit cards.

Although the present invention has been described in detail using specific embodiments, it is apparent to those skilled in the art that various modifications can be made without departing from the spirit and scope of the present invention.

The present application is based on Japanese Patent Application No. 2014-128330 filed Jun. 23, 2014, which is hereby incorporated by reference herein in its entirety.

REFERENCE SIGNS LIST

1: data acquiring apparatus
2: data managing apparatus
3: motion reproducing apparatus

The invention claimed is:

1. A motion reproducing system comprising:
a data acquiring apparatus acquiring human body motion data representing a human motion of a human patient during the motion, and transmitting the human body motion data;
a data managing apparatus receiving the human body motion data from the data acquiring apparatus, the data managing apparatus including a memory storing the human body motion data; and
a motion reproducing apparatus receiving the human body motion data stored in the memory from the data managing apparatus, and allowing the patient to reproduce the motion using the human body motion data, the motion being performed at the time of acquisition of the human body motion data,
wherein the data acquiring apparatus is a first wearable motion assisting apparatus including a first frame and a first drive unit, the first frame being worn along a portion between joints of a body of the patient and rotatably connected to the first drive unit, the first wearable motion assisting apparatus comprising:
a first biological signal detector detecting a biological signal generated in accordance with a motion of the patient;
a first angular sensor detecting a rotation angle of a joint corresponding to the motion of the patient;
a first torque sensor detecting an output torque of the first drive unit;
a relative force detector detecting a force acting on the first frame, the force being relatively determined by a relationship between the output torque of the first drive unit and a muscle force of the patient;
a first control unit calculating an assist force to be applied from the first drive unit to the first frame on the basis of the output torque of the first drive unit, the biological signal, the rotation angle, and the force acting on the first frame; and
a first communicating unit transmitting the output torque of the first drive unit, the biological signal, the rotation angle, and the force acting on the first frame as the human body motion data to the data managing apparatus;
wherein the motion reproducing apparatus is a second wearable motion assisting apparatus including a second frame and a second drive unit, the second frame being worn along a portion between joints of a body of the patient and rotatably connected to the second drive unit, the second wearable motion assisting apparatus comprising:
a second biological signal detector detecting a biological signal generated in accordance with a motion of the patient;
a second angular sensor detecting a rotation angle of a joint corresponding to the motion of the patient;
a second torque sensor detecting an output torque of the second drive unit;
a second communicating unit receiving the human body motion data from the data managing apparatus; and
a second control unit calculating an assist control output torque on the basis of, of the human body motion data, the output torque of the first drive unit, the biological signal detected by the first biological signal detector, the rotation angle detected by the first angular sensor, and the force acting on the first frame, calculating an angle control output torque for making equal the rotation angle detected by the first angular sensor and the rotation angle detected by the second angular sensor, and calculating an assist force to be applied from the second drive unit to the second frame on the basis of the assist control output torque and the angle control output torque;
wherein the second control unit calculates a force control output torque for making equal or proportional the output torque of the second drive unit and the output torque of the first drive unit included in the human body motion data, and calculates the assist force to be applied from the second drive unit to the second frame on the basis of the assist control output torque, the angle control output torque, and the force control output torque.

2. The motion reproducing system according to claim 1, wherein the data acquiring apparatus is a motion capture apparatus, and is configured to acquire a rotation angle of a joint of the subject as the body motion data.

3. The motion reproducing system according to claim 1, wherein the data managing apparatus includes a billing function unit configured to bill the motion reproducing apparatus when a request to send out the body motion data stored in the memory is received from the motion reproducing apparatus.

* * * * *